US009320270B2

(12) United States Patent
Casana Giner et al.

(10) Patent No.: US 9,320,270 B2
(45) Date of Patent: Apr. 26, 2016

(54) METHOD OF FIELD APPLICATION OF NATURAL PESTICIDES WITH REDUCED TOXICITY AND HIGH EFFICACY BY MEANS OF MICROENCAPSULATION

(71) Applicants: Victor Casana Giner, Ebenfurth (AT); Miguel Gimeno Sierra, Berndorf (AT); Barbara Gimeno Sierra, Berndorf (AT)

(72) Inventors: Victor Casana Giner, Ebenfurth (AT); Miguel Gimeno Sierra, Berndorf (AT); Barbara Gimeno Sierra, Berndorf (AT)

( * ) Notice: Subject to any disclaimer, the term of this patent is extended or adjusted under 35 U.S.C. 154(b) by 235 days.

(21) Appl. No.: 13/940,520

(22) Filed: Jul. 12, 2013

(65) Prior Publication Data

US 2014/0010854 A1 Jan. 9, 2014

Related U.S. Application Data

(62) Division of application No. 13/389,241, filed as application No. PCT/EP2009/005747 on Aug. 7, 2009.

(51) Int. Cl.
*A01N 25/28* (2006.01)
*A01N 43/90* (2006.01)
*A01N 25/30* (2006.01)

(52) U.S. Cl.
CPC ................ *A01N 25/28* (2013.01); *A01N 25/30* (2013.01); *A01N 43/90* (2013.01)

(58) Field of Classification Search
CPC ........ A01N 25/28; A01N 25/04; A01N 43/90
See application file for complete search history.

(56) References Cited

U.S. PATENT DOCUMENTS 6,426,082 B1 7/2002 Ueda et al.
2008/0306026 A1* 12/2008 Shirley et al. .................. 514/89

FOREIGN PATENT DOCUMENTS

WO WO2006089747 8/2006
WO WO2007039055 4/2007

OTHER PUBLICATIONS

Yuan, Qing-mei et al., Yunnan Daxue Xuebao, Ziran Kexueban (2005), 27(1), 57-59.*
International Search Report issued in connection with International Application No. PCT/EP2009/005747; completed Apr. 8, 2010, mailed Apr. 26, 2010, 2 pages.

* cited by examiner

*Primary Examiner* — Sue Liu
*Assistant Examiner* — Daniel Branson
(74) *Attorney, Agent, or Firm* — Vedder Price P.C.

(57) ABSTRACT

Microencapsulated formulations of macrolide lactones (abamectin, milbemectin, milbemycins emamectin, avermectins, ivermectins) wherein the active ingredient is protected from UV-degradation, with exceptional release characteristics resembling those of an emulsion concentrate or, if desired, of long-lasting effect; further with appropriate rheological properties, and with reduced toxicity. The invention provides a unique microencapsulation process for the chemical stability and biological activity of mectins, e.g. abamectin, and provides microcapsules of mectins to be used in formulations CS, WG/CS, ZC, EC/CS and any formulation type containing microcapsules and combination with other biologically active ingredients.

11 Claims, 9 Drawing Sheets

Figure 1.

Efficacy of the Microencapsulated Formulation according this invention (Capsule Suspension of Abamectin at 1.8 %; code ABM02-01) vs. Dynamec (Emulsion Concentrate of Abamectin at 1.8 %).

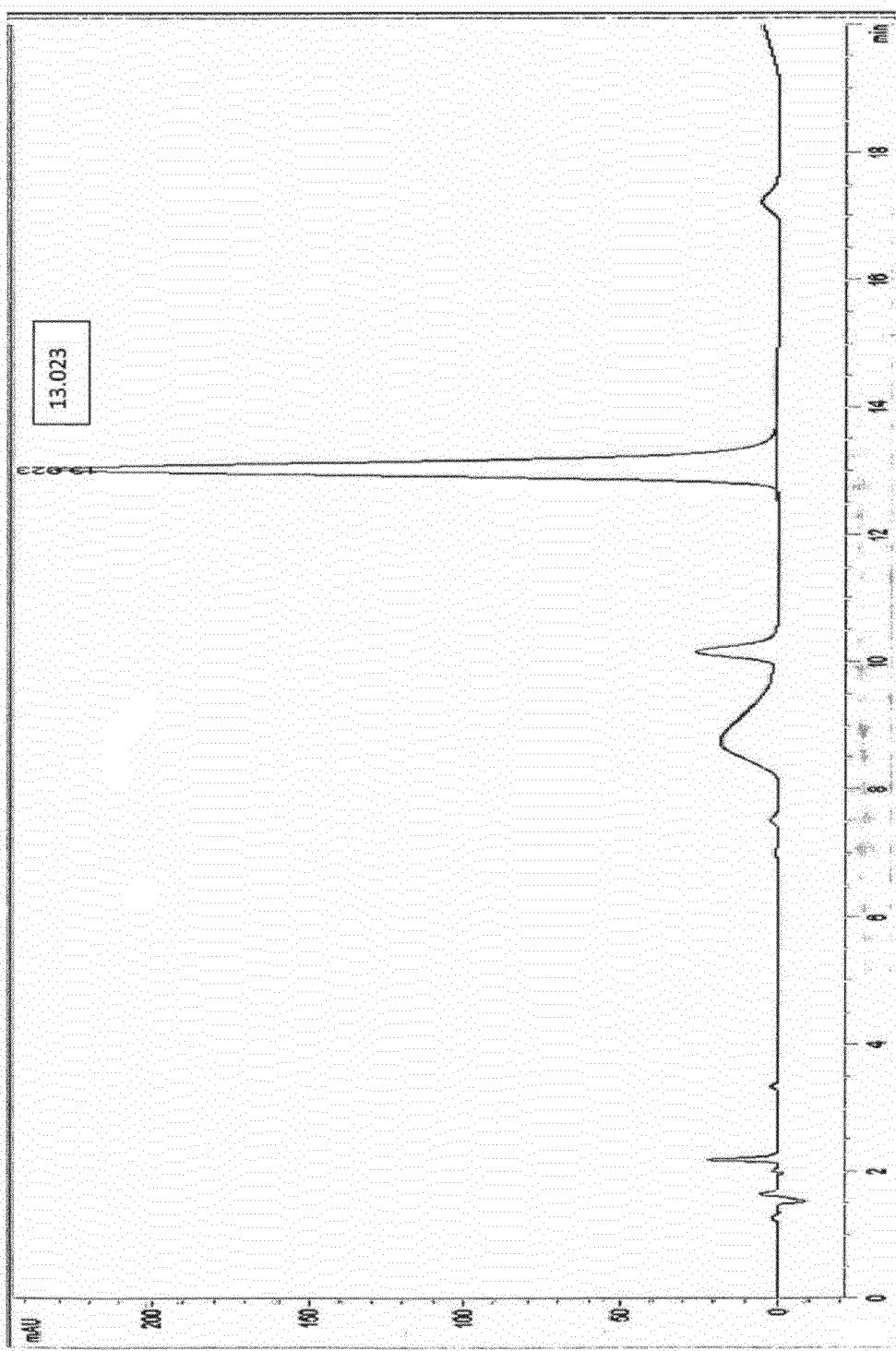

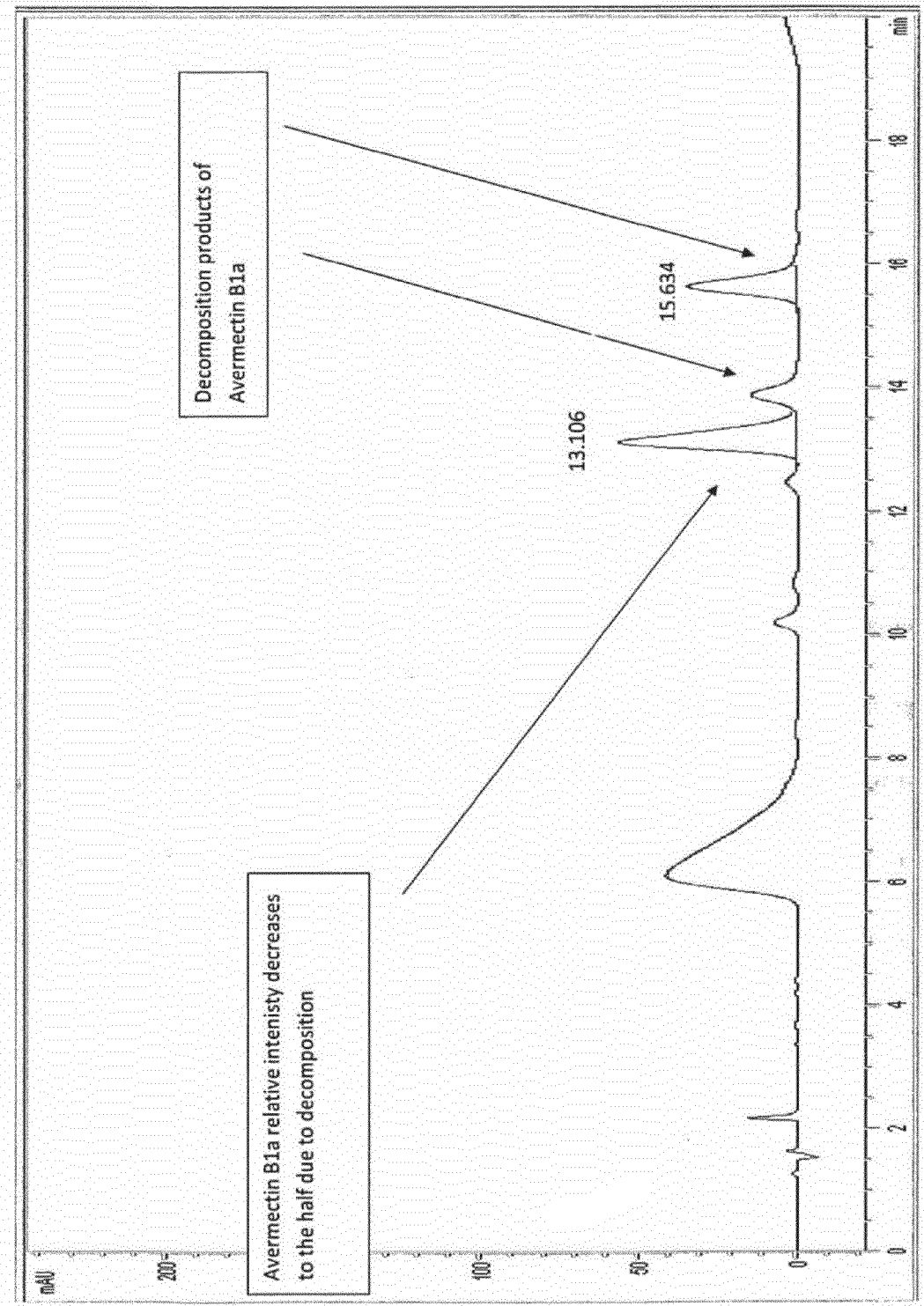

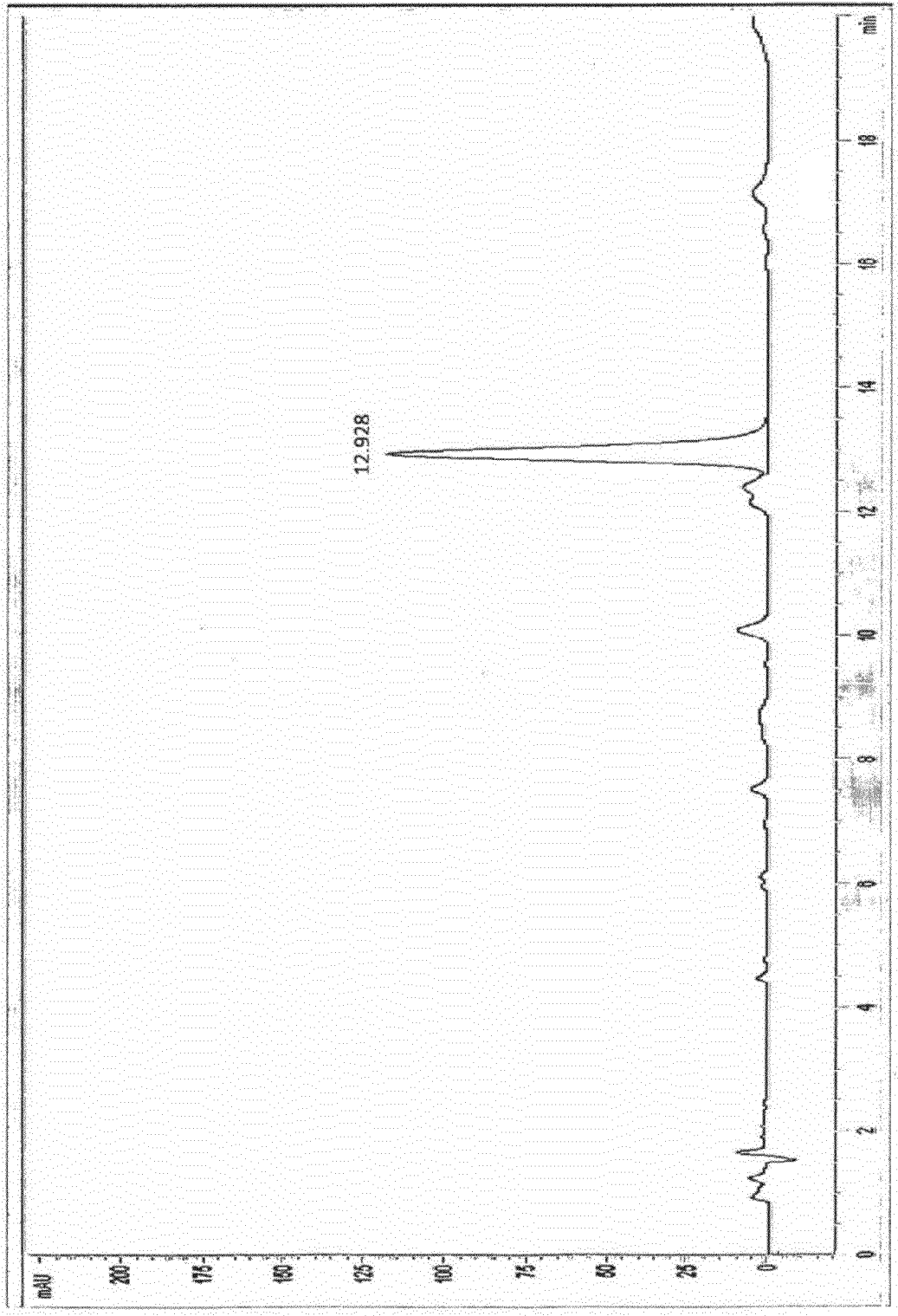

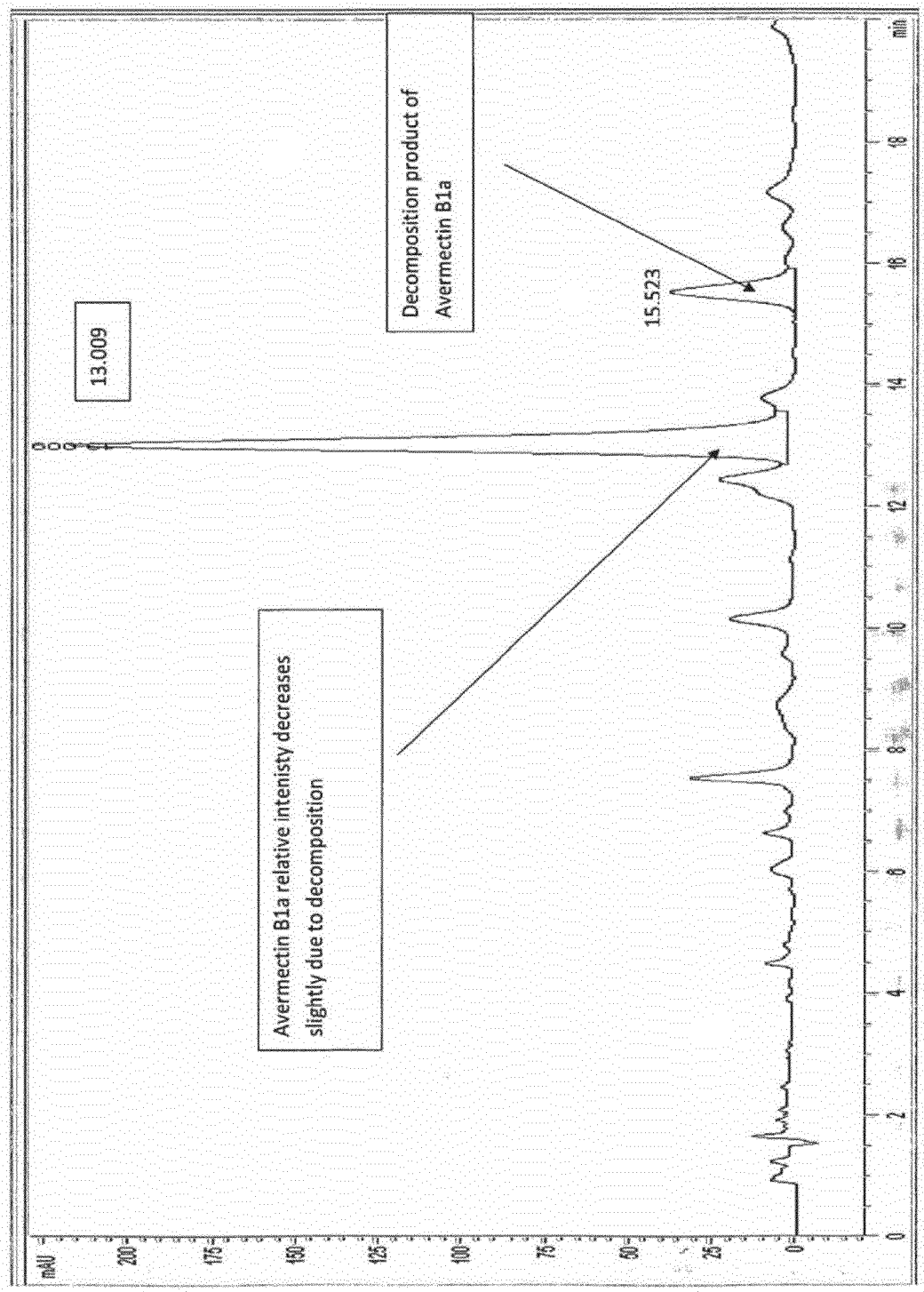

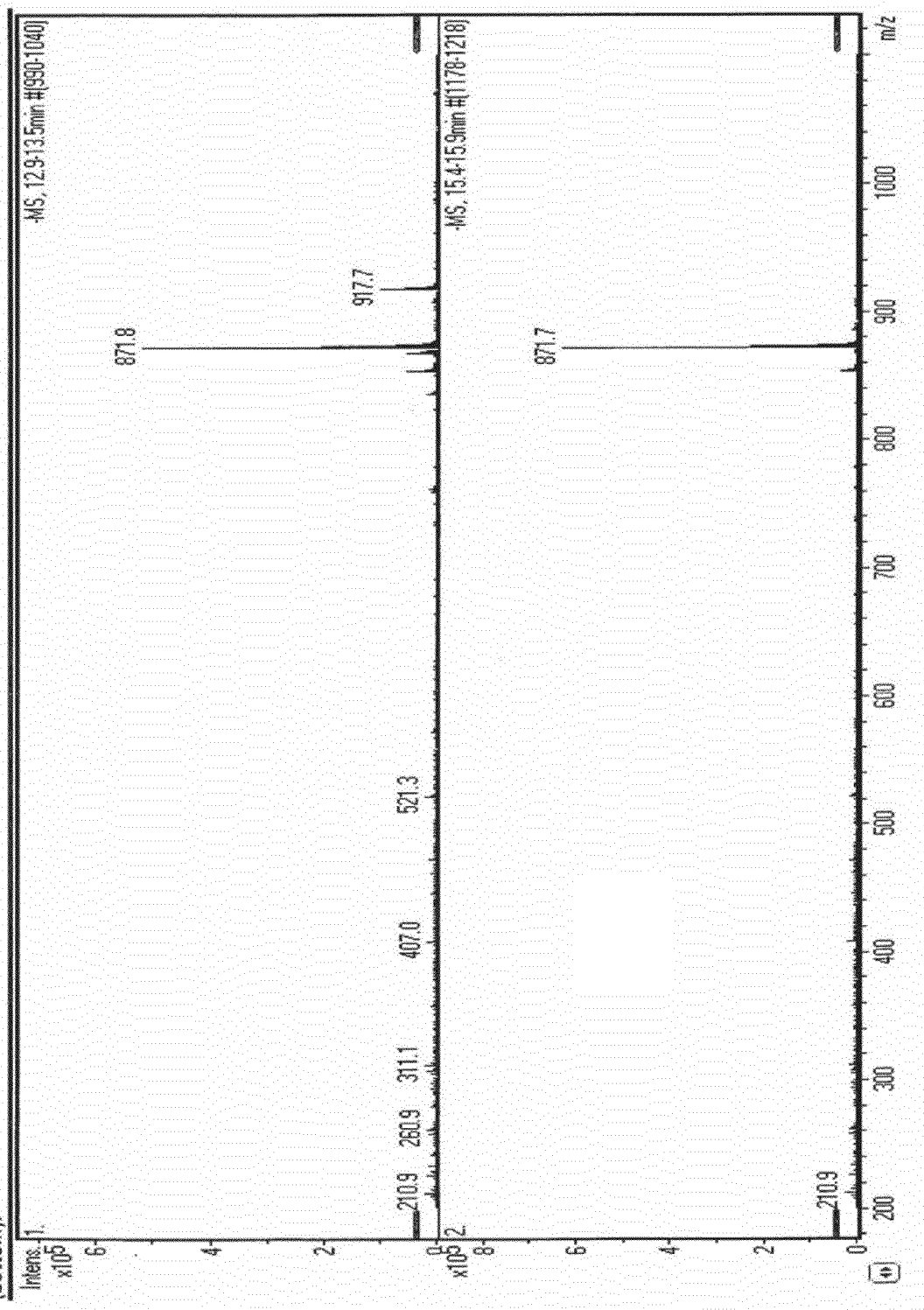

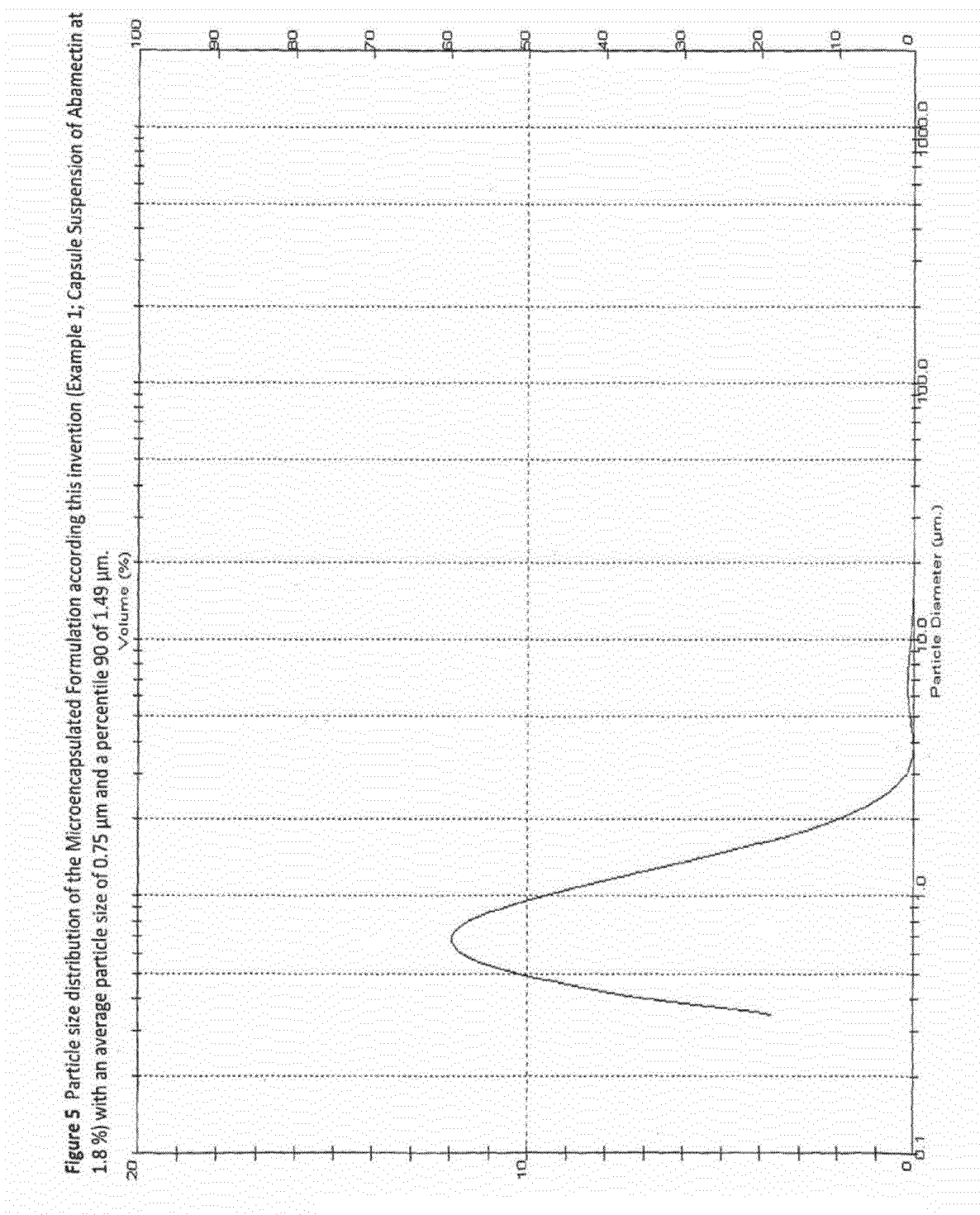
Figure 5 Particle size distribution of the Microencapsulated Formulation according this invention (Example 1: Capsule Suspension of Abamectin at 1.8 %) with an average particle size of 0.75 μm and a percentile 90 of 1.49 μm.

Figure 5 continuation

Result: Analysis Table

| | | | | |
|---|---|---|---|---|
| ID: KG02-240709 | | Run No: 5 | | Measured: 24.7.2009 12:16 |
| File: ABM02 | | Rec. No: 204 | | Analysed: 24.7.2009 12:16 |
| Path: C:\SIZER2\DATA\ | | | | Source: Analysed |

| | | | |
|---|---|---|---|
| Sampler: Internal | | Measured Beam Obscuration: 16.6 % | |
| Presentation: 4$$D | Analysis: Polydisperse | Residual: 0.609 % | |
| Modifications: None | | | |

| | | | |
|---|---|---|---|
| Conc. = 0.0021 %Vol | Density = 1.000 g/cm^3 | S.S.A.= 8.5882 m^2/g | |
| Distribution: Volume | D[4, 3] = 0.94 um | D[3, 2] = 0.70 um | |
| D(v, 0.1) = 0.42 um | D(v, 0.5) = 0.75 um | D(v, 0.9) = 1.49 um | |
| Span = 1.436E+00 | Uniformity = 5.444E-01 | | |

| Size (um) | Volume In % | Size (um) | Volume In % | Size (um) | Volume In % | Size (um) | Volume In % |
|---|---|---|---|---|---|---|---|
| 0.31 | 3.45 | 1.95 | 1.62 | 12.21 | 0.06 | 76.32 | 0.00 |
| 0.36 | 6.57 | 2.28 | 0.80 | 14.22 | 0.04 | 88.91 | 0.00 |
| 0.42 | 9.10 | 2.65 | 0.32 | 16.57 | 0.02 | 103.58 | 0.00 |
| 0.49 | 10.87 | 3.09 | 0.10 | 19.31 | 0.01 | 120.67 | 0.00 |
| 0.58 | 11.78 | 3.60 | 0.05 | 22.49 | 0.00 | 140.58 | 0.00 |
| 0.67 | 11.84 | 4.19 | 0.08 | 26.20 | 0.00 | 163.77 | 0.00 |
| 0.78 | 11.13 | 4.88 | 0.15 | 30.53 | 0.00 | 190.80 | 0.00 |
| 0.91 | 9.79 | 5.69 | 0.19 | 35.56 | 0.00 | 222.28 | 0.00 |
| 1.06 | 8.06 | 6.63 | 0.20 | 41.43 | 0.00 | 258.95 | 0.00 |
| 1.24 | 6.18 | 7.72 | 0.17 | 48.27 | 0.00 | 301.68 | 0.00 |
| 1.44 | 4.37 | 9.00 | 0.13 | 56.23 | 0.00 | | |
| 1.68 | 2.82 | 10.48 | 0.09 | 65.51 | 0.00 | | |
| 1.95 | | 12.21 | | 76.32 | 0.00 | | |

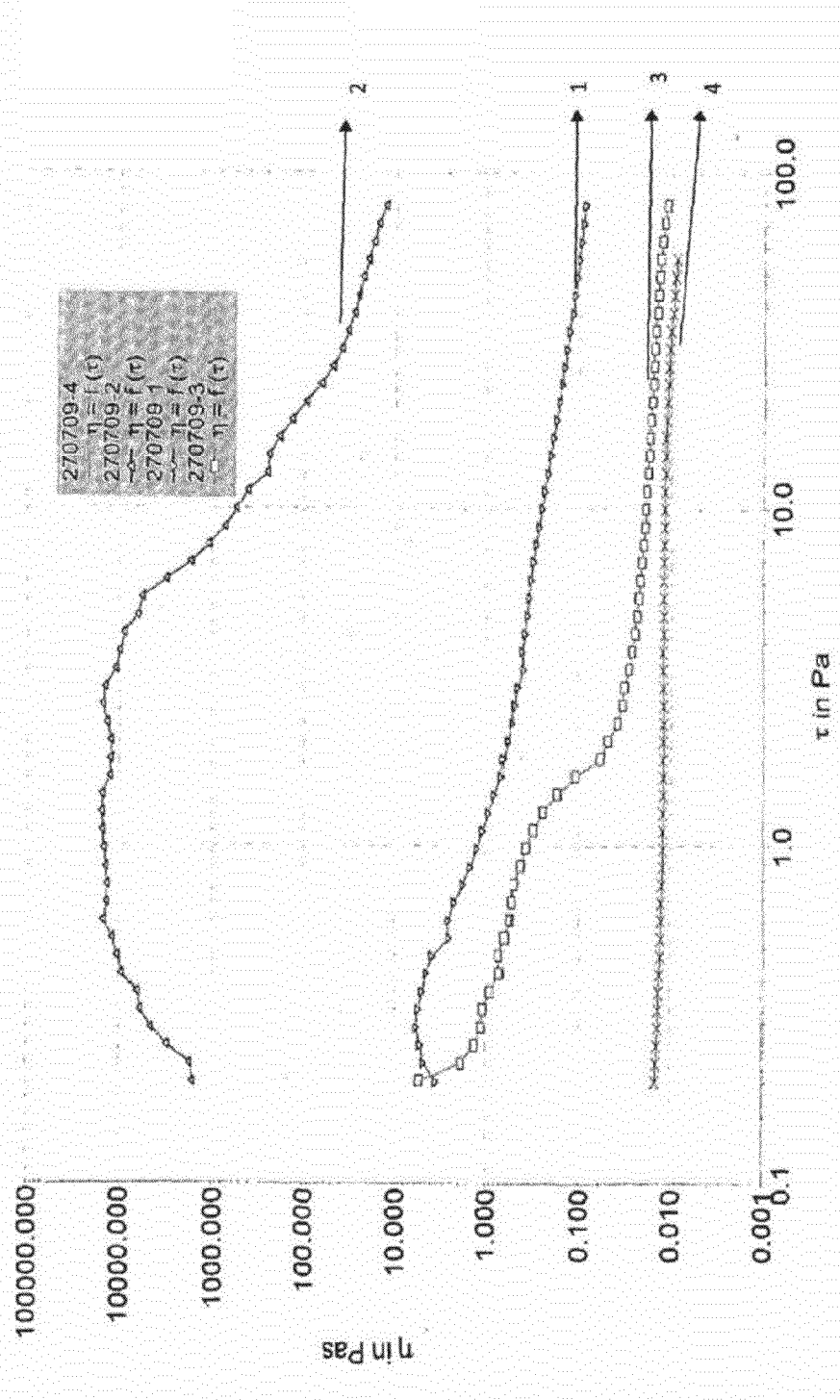
Figure 6 Rheological behavior of different formulations according the process of the invention with (1, 3) and without (2) the claimed coformulants after storage stability at 54 °C for 14 days; and when diluted in water (4).

METHOD OF FIELD APPLICATION OF NATURAL PESTICIDES WITH REDUCED TOXICITY AND HIGH EFFICACY BY MEANS OF MICROENCAPSULATION

RELATED APPLICATIONS

This application is a divisional application that claims priority to and the benefit of co-pending U.S. patent application Ser. No. 13/389,241, entitled "Microcapsules Containing Macrolide Lactones Abamectin, Milbemectin, Avermectins, Milbemycins, Emamectins, Ivermectins and Mectins in General," which was filed on Feb. 6, 2012, which is a National Stage Application of International Application No. PCT/EP2009/005747, which was filed Aug. 7, 2009, all the disclosures of which are incorporated herein by reference.

FIELD OF THE INVENTION

Microencapsulation of macrolide lactones, including avermectins, ivermectins, milbemycins (e.g., milbemicyn oxime), emamectins (e.g., emamectin benzoate), of microbial origin, preferably from *Streptomyces avermitilis, Streptomyces* spp., or synthetic, or DNA recombination origin.

STATE OF THE ART

The actinomycete *Streptomyces avermitilis* produces a series of chemically related compounds characterized for its helminticidal, miticidal, acaricidal and insecticidal properties, being the most representative group the avermectins (commercial product: Abamectin, that is a mixture of avermectin B1a and avermectin B1b). The first reports of their structure and particular antiparasitary activity go back to 1975; in particular Mrozik et al, disclosed their activity in Tetrahedron Letters (January 1983); 24 (48) pp. 5333-5336). The activity of the avermectins and the related compounds ivermectins and milbemycins is now believed to be due to altering the metabolism of gamma-aminobutyric acid and consequent neurological disturbances leading to death or reduced or suppressed reproduction. Such compounds may be produced as well by recombinant DNA techniques in other living beings, or even being chemically synthesized, preferably from an already formed backbone. The invention refers to all these compounds—all of them comprised under the term "mectins"—whether already disclosed or modifications still not disclosed (in so far is not altered its chemical behavior for the purposes of micro encapsulation).

Avermectins, and in general the "mectins" (a synonym used herein for the macrolide or macrocyclic lactones, normally with GABA activity), have two notorious characteristics: (a) they are sensitive to photodecomposition (b) they are relatively highly toxic by acute ingestion and inhalation, as shown by the some reported acute oral LD50 for rats of 10 mg/kg. Other helminticides or arthropodicides or biocides with even lower acute toxicology (e.g., carbofuran, alanycarb) are banned in some areas.

Further, the microencapsulation over 70% of the active ingredient is a problem still not solved, since the singular chemical characteristics of the mectins make them not directly suitable for conventional microencapsulation methods, as demonstrated by prior art publications.

The problem of photodecomposition and oxidation (as is the case the isomerization of abamectin to the 8,9-(Z) isomer and further photooxidation) may be addressed by different ways. Currently, abamectin is sold as an emulsion concentrate (EC) at a concentration of 18 g/L, and the problem of decomposition is solved by use of chemical antioxidants, as BHT. However, in the present invention, the protection of the mectins is solved by microencapsulation that per se offers protection against degradation, and for more protection, UV protectors are proposed to be used in both oil and water phases. Our microencapsulation materials and formula act specially well and synergistically with the use of certain types of surface active ingredients (e.g., alkenyl pirrolidinone dispersants). On the other hand, the toxicity for the human of the formulated mectins may be reduced greatly by means of microencapsulation: this effect can only be reached with a suitable level of entrapment of the mectins inside the microcapsules. In the literature, it is referred to microencapsulation levels only up to 65% (Yang, Kai et al.; Huagong Jinzhan (2005), 24(1). 65-67, 75) or to 84% (Yuan, Qing-mei at al., Yunnan Daxue Xuebao, Ziran Kexueban (2005), 27(1), 57-59); other documents do not show the level of microencapsulation and therefore the availability of the mectins to penetrate the body is increased with respect the present invention.

Since the effectiveness and dosage rates have been well optimized previously—1.8 g/L to 4 g/L is the concentration of choice in the case of abamectin as plant protection product—we prefer to focus in well known and safe concentration ranges. But, then, it is one of the problems addressed to imitate the efficacy pattern of an emulsion concentrate with a capsule suspension (CS). It is therefore the problem of the invention to solve simultaneously, but as well, individually the problems of i) elevated toxicity of the mectins ii) photodecomposition/oxidation of the mectins iii) controlled delivery (emulate the biological efficacy pattern of an emulsion concentrate of the same mectin (e.g., abamectin) while using the advantages of the microencapsulation or just to delay the release of abamectin for longer activity time) iv) obtain a functional capsule suspension formulation (or other types if further processed) complying with FAO/WHO standards in particular the huge problems of pourability and therefore associated viscosity and thixotropic characteristics associated with the microencapsulation of mectins.

While each of the problems addressed have been already object of several publications and patents, for other agrochemicals than mectins, there is no evidence, not even an enabling disclosure, that the advantages obtained herein have been achieved by any type of formulation or process.

All the problems i) to iv) are addressed herein, and solutions can be found for each individual problem and for all of them simultaneously.

The problem i) is solved by means of microencapsulation—for the toxicological part this is essential—done with a polymeric wall (preferably: polyurea, polyurethane, polyurea-polyurethane, polyurea-polyurethane-glycoluril, complex coacervates; resulting from the reaction of isocyanate resins, acrylic resins, complex coacervates) of the active ingredient(s) at a certain thickness of the wall (determined by the total wt.-% of wall forming materials and particle size) wherein the microcapsules have a mean diameter of 0.5-15 μm, preferably 0.7-2 μm (to have a high surface to release the mectin as similar as possible to an EC if the target is a fast release) or bigger sizes for slower release.

The closest state of the art is embodied by U.S. Pat. No. 6,955,823 (Syngenta Crop Protection Inc.) wherein in example 13 abamectin is microencapsulated at a concentration of 2%. The system contained 30% w/w oil phase; consisting of 18.7% w/w Solvesso, 4.7% w/w Decalin, 2% w/w Abamectin and encapsulation components: 3.2% w/w Beetle-80 and 1.4% w/w Q43; the aqueous phase contained 14.9% w/w Symperonic OP11 surfactant. Direct emulsification produced droplets in the 2-10 μm size range. The system underwent phase inversion at 41° C. The encapsulated dispersion had a bimodal size distribution with peaks at 200 nm and 25 μm (far different to the distribution obtained by our invention). It is notably that such document is one of the very few that makes an enabling disclosure of how to microencapsulate abamectin. Regarding the particle size, the prior art does not preferably choose the range that we designate as the most appropriate for our purposes, rather, U.S. Pat. No. 6,955,823 points out to the skilled in the art to go simultaneously below and above of our purposively selected particle size (0.5-150, in the case of trying to simulate the biological and field efficacy of an emulsion concentrate (EC). Lesser to achieve the homogeneicity of the microcapsules (leptokurtic distribution) that we have obtained. The formulation of microcapsules of U.S. Pat. No. 6,955,823 do not contain any specific antioxidant and/or UV-protectant, thus leading away the skilled in the art to adopt some features of our invention. Further, nothing is said regarding the release profile and the influence of the carbohydrate hydrocolloids in such release rata—we observed that at least a gum must be present—; either regarding the stability of the formulation containing such colloids in the ranges as we claim. While other features are shared in this invention and the closest prior art (as the use of an oil soluble surfactant with HLB from 6-14), there are essential differences that lead in no way obviously to the results looked for by the inventors of the present invention. Of the millions of the combinations that are possible to make a microencapsulated formulation of agrochemicals at the view of the prior art, it is impossible to arrive to the purposive and narrow selection of ingredients and percentages we propose; even lesser to the problems that we address. For example, reading Ma, Li-jie et al., Beijing Huagong Daxue Xuebao, Ziran Kexueban (2006), 33(6), 51-56; the microencapsulation of avermectins would need the use of the surfactants Tween 80 and Span 20. Reading the aforementioned paper of Yang Kai, the skilled in the art would try to use complex coacervation (gelatin and Arabic gum) as the best solution and still, it would get only 65% of effective entrapment of abamectin inside the microcapsules. On the other side, according Yuan Quing-mei, the encapsulation efficiency would be still only 83.24%, with no hint regarding the emulation of the activity as emulsion concentrate at high encapsulation yields (as we do in our invention over 90%). Our invention, obviously may be used for extending the release time by means of increasing the particle size and quantity of microencapsulated material, problem much more easy to handle than a fast effect of a microencapsulated abamectin.

BRIEF DESCRIPTION OF THE DRAWINGS

FIG. 1 illustrates an efficacy of an embodiment disclosed herein.

FIG. 2A illustrates an emulsion concentration of Abamectin at 1.8% at time=0 hours.

FIG. 2B illustrates an emulsion concentration of Abamectin at 1.8% at time=64 hours.

FIG. 3A illustrates a microencapsulated formulation embodiment as disclosed herein at time=0 hours FIG. 3B illustrates a microencapsulated formulation embodiment as disclosed herein at time=64 hours.

FIG. 4 illustrates a mass spectra distribution of Abamectin B11 and of main decomposition product (Z-8, 9 issues) corresponding to a peak at 15.5 min. of FIG. 2B.

FIG. 5 illustrates particle size distribution of one formulation embodiment disclosed herein.

FIG. 6 illustrates the rheological behavior of different formulations according to one embodiment of a process disclosed herein.

DESCRIPTION

Our microencapsulated mectins are characterized in that the suspension of microcapsules contain, expressed in total weight percentages with respect to the total weight of the formulation—as not limiting example and adapted to one of the many applications of the invention, namely, for plant protection products—:

a. At least one macrolide lactone active ingredient compound at 0.1-40%, preferably at 1-10%, wherein the ration macrolide lactone and gum(s) is from 10:1 to 1:20; wherein for easier microencapsulation it is better to dissolve it in any agrochemical suitable solvent wherein the abamectin is fully dissolved, as vegetable or animal oils, modified (esterified, etherified, methylated, hydrogenated, etc.) vegetable or animal oils—as corn or soybean oil, methyl cocoate—, functionalized oils as branched or linear alcohols or polyalcohols or carboxylic acids, waxes, rosin gums or other gums if necessary mixed with other oils for fluidity, naptha solvents preferably naphthalene depleted, paraffinic oils, modified or functionalized paraffins, fatty acids and derivatives thereof, alcohol/alkoxyphosphated oils (e.g., ethanol/2-butoxyphosphate at 3:1 ratio), and any other lipophilic substance inert to the rest of the formulation ingredients that is able to dissolve the mectins, or mixtures thereof. The preferred oil is such oil wherein the macrolide lactone is completely dissolved at the concentration used, it is soluble in water only up to 50 g/L and has at least a polar moiety as hydroxyl, sulfate, phosphate, carboxylic acid, ester, amine, amide, peptidic bonds or belongs to the group of alkoxy phosphates. Most preferably, the oil is Hostaphat® B310 or equivalent product. The use of naphtha solvents, on the other hand, showed to be the less convenient election of solvents within the most used in plant protection products.
b. The wall of the microcapsules is made of a polymeric material at 0.1-35%, preferably at 1-3% for fast release microcapsules simulating an EC formulation or 5-20% for long lasting release;
c. The average size of the microcapsules is from 0.5-50 μm; preferably 0.5-2 μm and a percentile 90 below 10 μm for fast release formulations and from 10-50 μm for slow release formulations;
d. The water phase contains at least:
    i. one or more carbohydrate hydrocolloid(s) and/or derivative thereof at 0.1-30%, preferably a combination of two hydrocolloids at a ratio 1:20 to 20:1, preferably consisting in Arabic gum and Xanthan Gum, preferably from 0.1-3% of the formulation and at a ratio 10:1. Arabic gum best ratios are at 0.25-3% and Xanthan gum at 0.1-3%. and
    ii. one or more surface active compound(s) at 0.3-3 0%; selected from a) and/or b):
        a. an alkaline or alkaline-earth salt that contains naphthalene sulfonate, lignosulfonate, sulfomethylated lignosulfonate or succinate, sulfosuccinate groups; and/or derivatives thereof; preferably sulfomethylated lignosulfonates at 1-5% and/or
        b. a dispersant of the type alkenyl or alkanyl or alkylen pyrrolidinone polymer and/or derivatives thereof; preferably a 1-ethenyl-2-pyrrolidinone homocopolymer with ethanol or isopropanol;

wherein a)+b) is from 0.3% to a ratio a)+b): corresponding macrolide lactone(s) of 50:1 and preferably containing as well a block copolymer of ethylene oxide and propylene oxide of 10 to 100 mols apart from the compounds ii. a. and b. This way, the percentage of microencapsulated macrolide lactone(s) as per a. is at least 90%, this being tested by centrifugation with consequent weight percent quantification by HPLC-UV or HPLC-MS;

e. Additional customary coformulants if and as needed depending on the final use of the suspension, as they are pH regulators, acidulants, silicates, clays, aluminosilicates, other viscosity modifiers, antimicrobial agents, UV protectors, antioxidants, antifoams, safeners, antifreezing agents as glycols, preferably propylenglycol, diethylenglycol, polypropylenglycol, polyethylene glycol and similars, etc., at a concentration of 0.2-20% preferably 1-7% and most preferably at 2-5%.

Further, the formulation may contain in the water phase or microencapsulated oil phase other biologically active ingredients, preferably helminticides, nematocides, acaricides, miticides, insecticides, but also with herbicides, fungicides, plant growth regulators, bactericides (antibiotics) etc.; the biocides for small animals preferably selected from the list, as non-limiting example: (1) organoptsphorous compounds as acephate, azinphosmethyl, cadusafos, chlorethoxyfos, chlorpyrifos, coumaphos, dematon, demeton-5-methyl, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion, mevinphos, monocrotophos, parathion, phorate, phosalone, phosmet, phosphamidon, phosphocarb, phoxim, profenofos, propaphos, propetamphos, prothiofos, pyrimiphos-methyl, pyrimiphos-ethyl, quinalphos, sulprofos; tebupirimphos, temephos, terbufos, tetrachlorvinphos, thiafenox, thiometon, triazophos, and trichlorphon; (2) carbamates such as aldicarb, bendiocarb, benfuracarb, bensultap, BPMC, butoxycarbocim, carbaryl, carbofuran, carbosulfan, cloethocarb, ethiofencarb, fenobucarb, furathiocarb, methiocarb, isoprocarb, methomyl, oxamyl, pirimicarb, promecarb, propoxur, thiodicarb, and thiofurox; (3) pyrethroids such as acrinathrin, allethrin, beta-cyfluthrin, bifenthrin, bioresmethrin, cyfluthrin; cyhalothrin; lambda-cyhalothrin; gammacyhalothrin, cypermethrin; alpha-cypermethrin; zeta-cypermethrin; deltamethrin, esfenvalerate, fenvalerate, fenfluthrin, fenpropathrin, flucythrinate, flumethrin, fluvalinate, tau-fluvalinate, halfenprox, permethrin, protrifenbute, resmethrin, silafluofen, tefluthrin, tetramethrin, tralomethin, fish safe pyrethroids for example ethofenprox, natural pyrethrin, tetramethrin, s-bioallethrin, fenfluthrin and prallethrin; (4) acylureas, other types of insect growth regulators and insect hormone analogs such as buprofezin, chromfenozide, chlorfluazuron, diflubenzuron, fenoxycarb, flufenoxuron, halofenozide, hexaflumuron, hydroprene, lufenuron, methoprene, methoxyfenozide, novaluron, pyriproxyfen, teflubenzuron and tebufenozide, N-[3,5-dichloro-2-fluoro-4-(1,1,2,3,3,3-hexafluoropropoxy)phenyi]-N'(2,6-difluorobenzoyl)urea; (5) neonicotnioids and other nicotinics such as acetamiprid, AKD-1022, cartap, TI-435, clothianidin, MTI-446, dinotefuran, imidacloprid, nicotine, nitenpyram, thiamethoxam, thiacloprid; (6) macrolides such as avermectins, milbemycins, for example such as abamectin, ivermectin, milbemycin, emamectin benzoate; and (7) other insecticidal, acaricidal, mollusquicidal and nematocidal compounds or actives such as aldrin, amitraz, azadirachtin, azocyclotin, bifenazate, bromopropylate, chlordimeform, chlorfenapyr, clofentezine, chlorobenzilate, chlordane, cyhexatin, cyromazin, DDT, dicofol, dieldrin, DNOC, endosulfan, ethoxazole, fenazaquin, fenbutatin oxide, fenproximate, beta-fenpyroximate, fipronil, flubenzimine, hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulfur, tebufenpyrad, tetradifon, triazamate, an insect-active extract from a plant; a preparation containing insect-active nematodes, a preparation obtainable from *Bacillus subtilis, Bacillus thuringiensis*, a nuclear polyhedrosis virus, or other like organism genetically modified or native, as well as synergists such as piperonyl butoxide, sesamax, safroxan and dodecyl imidazole.

Preferably, the mectins are combined with at least one compound selected from: imidacloprid, acetamiprid, thiamethoxam, thiacloprid, nitenpyram, dinetofuran, clothianidin. Particularly interesting are the combinations imidacloprid and abamectin, as well as acetamiprid and abamectin, thiamethoxam and abamectin, thiacloprid and abamectin and clothianidin and abamectin; preferably formulations wherein the abamectin is at 1-5% and the neonicotioid at 5-20%.

Of course, the presence of additional mectins or other active ingredients may be inside the microcapsules (in the oil phase entrapped by the microcapsule's wall) or outside as suspension concentrates (namely, a suspoemulsion ZC formulation). Even the microencapsulated mectins (with or without additional active ingredients) may be spray dried and suspended in an continuous oil phase, or just extruded or spray dried (to form a water dispersable granules of capsules (WG/CS)), and other combinations of formulations state of the art.

We have observed that the formulations according what is described above show excellent physicochemical properties and a tailored release rate. Further, the level of effective microencapsulation is never below 87% (namely, at the most 12.4% of the mectins remain outside of the microcapsules), and in some best cases, it reaches 99.7% of effective microencapsulation, a difference over state of the art microcapsules. It is considered that to avoid an adequate reduction of the dermal and acute toxicity, the level of microencapsulation must be at least 90%, otherwise the moderately toxic abamectin may cause handling problems, that for many other agrochemicals would not be necessary, but it is for abamectin due to its relative elevated toxicity. The best effective microencapsulation happens especially with the use of a mixed polymeric wall of isocyanates and glycoluril alkoxyalkyl derivatives, therefore we particularly claim suspension of microcapsules according the aforementioned characteristics wherein the wall forming material is made of the result of an in-situ/interfacial polymerization of isocyanates and glycoluril derivatives and/or made of the result of an polymerization of monomers leading to polyurea, polyurea-polyurethane, polyurethane, polyurea-polyurethane-glycoluril mixed polymer. This is achieved better with the use of aminofunctional catalysts, optionally with the concomitant use of bibutyltindilaurate, ethylenediamine and sulfonic acids, the latter accelerating the incorporation of the glycolurils into the wall. By FT-IR investigation on isolated and dried microcapsules, we can determine that the lignosulfonates used in the formulation are not covalently attached to the walls, to the difference of other preliminary publications where this incorporation of the lignosulfonates direct into (not onto) the structure of the wall provides UV protection. In our case, the lignosulfonates or other substituting compounds as describe below help for a correct emulsification and encapsulation; that moreover have a synergistic effect on UV protection with the simple microencapsulation.

The inventors have realized that the problem of mectin's photodecomposition/oxidation has been underestimated: while a highly pure technical may appear very suitable to be formulated, it is the case that during the shelf life of the product, a multiplicity of still not identified decomposition products with unknown toxicological profile (but certainly likely to be much less toxic than the parent mectins). This can be highly reduced with the microencapsulation together with the use of the proposed protective colloids and surface active agents (two distinct carbohydrates and the lignosulfonates/napthalenes/succinates). However, additional to the referred protective UV action of our microcapsules, the use of a combination of two different UV-protectors and two different antioxidants, the decomposition of the mectins, in particular abamectin, is almost negligible and prolongues the shelf life of the product. The best choice is to use an UV-protector in the water phase (dispersed or water soluble) and another one in the oil phase, close to the active mectins. We prefer the use of Escalol® Series (Escalol 557 in the water phase and Escalol 507 in the oil phase), because they showed the best results, although any inorganic or organic UV-blocker, reflectant, dye, absorbant, or in some way protector may be used, as titanium dioxide or zinc oxide (preferably in the oil phase and coated with a protective layer to avoid the contrary effect of photooxidation), carbon black, dyes, inks, etc. The protection of mectins is maximum when additionally a water soluble antioxidant is in the water phase (as ascorbic acid) and an oil soluble antioxidant is in the oil phase (as BHT, BHA, vitamin E, tocopherols, tocotrienols, ascorbyl palmitate and/or stearate and/or laurate, etc.), and most preferably two of these oil antioxidants are present in the oil phase.

The UV-protectants (total quantity if used in combinations) preferably are at 0.05-10% and the total antioxidants at 0.05-10%.

The use of the mentioned formulations of mectins (optionally combined with other agrochemicals) is preferably against—but not limited to—: *Capopsylla pyri, Capopsylla, Psilidae* gen. sp., *Cydia pomonella, Phtorimaea operculella, Phtorimaea* spp., *Plutella xylostella, Plutella* sp., *Tetranychus urticae, Tetranychus kanzawai, Tetranychus* ssp., *Panonychus citri, Panonychus* ssp., *Panonychus* spp., *Aculops pelekassi, Aculops* spp., *Bursaphelenchus xylophilus, Bursaphelenchus* ssp., *Liriomyza huidobrensis, Liriomyza trifolii, liriomyza* spp.; and leaf miners, red spiders, and sucking arthropods in general.

An aspect that is necessary to consider when using the invention for agricultural purposes is that the rheology of the formulation must be well controlled, since the formation of complex liquid crystal structures when the product stands for some period of time without any agitation leads to problems of thixotropy and consequent problems to empty the agrochemical canisters (pourability problems, increase of viscosity with time). Although this effects may be reversible with some shaking of the formulation (suspension of microcapsules or other microcapsule's formulations as mentioned above), the farmers do not necessarily perform this operation. For this reason, we have adjusted the content of the viscosity modifiers (and the nature) and in general, the whole formulation to obtain the results that we show in the Examples section.

The general process of microencapsulation is as follows:
a. A first water phase is prepared with water, at least one hydrocolloid, at least one lignosulfonate or derivative thereof, a pH stabilizer preferably that has as well antioxidant properties, as ascorbic acid, and optionally a water soluble or emulsifiable or dispersible UV-protectant and if needed customary coformulants as viscosity modifiers or surfactants that will result in an improve stability of the emulsion once the farmer mixes the concentrate in the spray-tank water;

b. An oil phase is prepared with a water-immiscible solvent able to dissolve the targeted amount of the macrolide lactone, a mixture of wall forming materials, at least an oil soluble or emulsifiable or dispersible catalyst able to trigger the polymeric formation of the wall, preferably an alkyl tin fatty acid ester preferably previously dissolved in an oil solvent, optionally the same that dissolves the mectins, and a functional amine (ethylenamine, ethylendiamine, hexamethlenamine, triethylamine, cyclic azepins, etc.) an optionally an oil soluble antioxidant, an oil soluble UV-protector and the mectin active ingredient (macrolide lactone);

c. The oil phase is emulsified into the water phase at about 50° C. under high shear stress;

d. According to the desired strength of the wall a secondary catalyst of the type functional amine may be added to the emulsion resulting of c., ten to thirty minutes after c. and optionally a sulfonic acid to reach a pH below 5.1 but above 3.5 to avoid decomposition of the mectins(s);

e. About 10-30 minutes after d., a secondary water phase may be added under gentle stirring to the solution resulting from d. if the final use of the suspension needs a high stability regarding dispersion at long shelf lige, containing water, at least one emulsifier of HLB 6 to 14, preferably a block copolymer of ethylene oxide and propylene oxide, a lignosulfonate, and optionally a disperant different from a lignosulfonate;

f. A period of hardening of the microcapsules under gentle stirring is performed until the wall forming reactions have been completed, at about 50-70° C. in a first period and then letting the solution to cool down to room temperature;

g. A tertiary water phase is prepared containing water, viscosity modifier agent, a second carbohydrate colloid, preferably a gum, a polyglycol and eventually customary agriculturally additives; being added after step e. under gentle agitation;

h. The solution resulting after step g. is ready for packaging and use by the costumer.

i. Eventually mixing the solution resulting after step g. with other agrochemical formulation types to perform other formulation types different than capsule suspension (CS) as ZX or ZC formulations, and eventually drying the CS or mixtures thereof, to produce WG/CS, and/or eventually microencapsulating the resulting suspension in an oil based media wherein the water phase and the macrolide lactone-containing microcapsules are microencapsulated and suspended in the continuous oil-phase.

In brief, the following invention, independently from the ingredients, has shown that the inventors have been capable of perform microencapsulated formulations of macrolide lactones consisting of a suspension of microcapsules enclosing at least one macrolide lactone microencapsulated in microcapsules of an average particle size of 0.5-2.5 µm and a percentile 90 below 15 µm, for achieving simultaneously in plant protection products:

a. To reduce the dermal and acute oral toxicity when compared to an emulsion concentrate of the same macrolide lactone(s) at the same concentration;

b. To reduce the UV and visible light degradation when compared to an emulsion concentrate of the same macrolide lactone(s) at the same concentration;

c. To achieve a biological effect (speed and activity pattern against undesirable organisms) comparable to that of an emulsion concentrate of the same macrolide lactone(s) at the same concentration.

Since this effects have never been addressed either achieved before, it is claimed such type of formulations, that still have no similarity in any commercial product regarding the extremely narrow and homogeneous size of the microcapsules—that indeed allows the fast and homogeneous release of the mectin, thus mimicking an emulsion concentrate at the same concentration of mectin—, and the protection from light of the mectins.

The following examples will allow the skilled in the art to reproduce the invention, considering that for obtaining different release rates, the quantity and quality of wall forming material must be changed (e.g., complex coacervates will release the mectins faster than the polyureas).

EXAMPLES

In this section we show our preferred embodiment, as well as comparisons with different formulations, discussed with regard the advantages of the present invention.

Preferred Embodiment

Example 1

A formulation of abamectin at 1.83% (minus the impurities of the technical) is prepared according the process of the invention and with the following ingredients:

|  | Parts |
|---|---|
| Abamectin | 1.83 |
| TEGO MR2138 | 0.49 |
| Agrimer ® VA6 | 2.00 |
| Arabic Gum | 1.01 |
| Ascorbic acid | 0.49 |
| Atlox 4913 | 3.00 |
| BHA | 1.00 |
| Dibutyltindilaurate | 0.00 |
| Escalol ® 507 | 0.60 |
| Escalol ® 577 | 0.52 |
| 1,6-Hexanediamine | 0.30 |
| Germall ® II | 0.20 |
| Hostaphat ® B310 | 40.20 |
| Powderlink ® 1174 | 1.60 |
| Diethylenglycol | 3.35 |
| Reax 85 A | 2.99 |
| PAPI ® | 2.00 |
| Synperonic PE/L64 | 2.00 |
| TMXDI ® | 1.14 |
| Water | 35.10 |
| Xanthan Gum | 0.20 |

In a first step, it is prepared an oil phase (about 35 parts) with Hostaphat 8310 (2-butoxyphosphate/ethanol at 1:3 ratio), Abamectin (macrolide lactone), Escalol 507 (oil soluble UV-protector), BHA (butylhydroxyanisol) dibutiltinlaurate (catalyst dissolved in Hostaphat 8310 at 1%), and the wall forming materials PAPI (polymethylenepolyphenyl isocianate), TMXDI (m-tetrametyhlxylene diisocyanate) and Powderlink 1174 (tetramethoxymethyl glycolrulil). If any other active ingredient(s) substantially insoluble in water is desired to be as well microencapsulated, it must be added to such oil phase, or, eventually if they are water soluble, dispersed in the oil phase with appropriate dispersants that will prevent its (their) transfer to the water phase.

Then, a first water phase (about 30 parts) is prepared containing water, TEGO MR2138 (silicon antifoam), Escalol 557 (water soluble/dispersible UV-protector), Agrimer VA6 (1-ethenyl-2-pyrrolodinone ester), Arabic Gum, Reax 85 A (disodium sulfite and formaldehyde reaction product with lignin), and ascorbic acid.

The process of microencapsulation is performed adding the oil phase to the first water phase under high shear stress, being emulsified at 70° C. (we observed that he temperature of emulsification does not affect the stability of the mectins in so far there are present antioxidants and weak acids; otherwise, the abamectin undergoes decomposition (5-25%), and then, the temperature of emulsification must be at or below 50-55° C. to avoid this fact; since the use of these compounds is beneficial for other properties at long term, it is recommended to use them right here).

The emulsion is left for a period of 30 to 4 hours, preferably 1 hour at this temperature and gentle anchor stirring, since the high shear stress must be applied only until the emulsion is formed.

Although the suspension of microcapsules is already finished, and usable for certain purposes (as to mix it with a suspension concentrate, emulsify it into an emulsion concentrate or re-encapsulate it in a new continuous oil phase), for plant protection products it is needed to add further coformulants.

For this reason a second water phase (about 11 parts) is added containing further lignosulfonates in the similar quantity as above, further non-ionic surfactant(s) (Atlox 4913, in propylene glycol, and a block copolymer ethoxylated-propoxylated with molecular weight and additional carbohydrate hydrocolloid). The is distribution of coformulants after and before the microencapsulation provide a very good help into reducing the viscosity during the microencapsulation step and therefore to obtain the extremely reduced particle size. After the addition of this second water phase, a similar cooking time (at the temperature used in the step above) is carried out. In this step, if wanting to obtain a stronger wall, it is added a functional amine, as hexamethylendiamine (such amines emulsified and/or dissolved in water).

Finally the suspension is adjusted with a third water phase (about 15 parts) wherein a second carbohydrate hydrocolloid is present (in our example, Xanthan Gum), plus, if desired, a biocide (Germall II) and an antifreezing agent (diethylengly-col). Optionally it can be added at this step suspending agents and viscosity modifiers as aluminosilicates, silicates and any other compounds with this function.

The formulation, already finished, is let to cool down at room temperature.

Examples and Conclusions Regarding Efficiency of Entrapment and Reduction of Toxicity of our Invention.

The formulation of the example shows that the percentage of microencapsulated abamectin is 97.7%. To measure this, the formulation is diluted in water; optionally containing sucrose at a total density equal to the density of the mectin to be measured—1:1 ratio of formulation:water—(to avoid that in the centrifugation process the mectin makes a density gradient in the vial and stays on the bottom preferentially) and it is cetrifuged at 4500 rpm in a conventional biochemistry ultracentrifuge for 20 minutes. The upper phase is separated from the precipitated capsules and the capsules are rinsed with water twice on a filter of 0.3 µm. The solid residue is disregarded and the extration, together with the upper phase are extracted with toluene and such extracted part is submitted to HPLC-UV chromatography to quantify exactly the free abamectin not microencapsulated. According U.S. Pat. No. 6,955,823—repeated as far as we could follow the exact microencapsulation method, and obtaining a bimodal distribution of the microcapsules but with approximately 1.5 size as those claimed—the amount of free abamectin in U.S. Pat. No. 6,955,823 is 16.3%, in front of our extremely low value of 2.3%. Notably, when using naphtha oils or parafinnic oils the level of microencapsulation is as discussed above, complex coacervation methods achieve only a effective microencapsulation of less than 84%. Therefore, and according theoretical considerations in toxicology—experimental proofs ongoing at the time of writing this document, our invention provides a significant reduction of the dermal and acute ingestion toxicity of the product abamectin, whichever theoretical toxicology model is used to perform this evaluation from a theoretical/semiempiric point of view.

Notably, when the Hostaphat B310 is not used, and according to our invention, other oils are used, as methyl cocoate, the ranges of entrapment are still absolutely satisfactory, but statistically significantly reduced (90.1% for methyl cocoate, 91.5% for corn oil, 93.1% for Solvesso 150 ND). The use of at least 40% of Hostaphat B310 provided in all cases levels of entrapment over 94% (with the same oils as in the previous sentence mixed with it).

Examples and Conclusions Regarding Particle Size of the Microcapsules and Homogeneicity to Achieve Targeted Release Patterns.

Surprisively, when using the compounds as described in the claim, in order to get particle sizes so difficult to get industrially as in the embodiment of this invention for fast release (as an average particle size of 0.54 µm, and a percentile 90 of 12.31 µm as was the case in this example) there is no need to use higher shear stress equipment or speeds: the components of the suspension of microencapsulated mectins as claimed in this invention allow the formation of extremely small and regular particle sizes that is impossible to get with state of the art methods of microencapsulation, in particular those described for abamectin. Note that the Syngenta's process cited above, obtains sizes below 0.5 µm, but at the same time there is a bimodal distribution with substantially higher particle sizes, circumstance not happening according to the present invention. Bimodal distributions let not easily predict the behavior of the formulation against the targeted animals. In our example we have embodied the formulation according to the present invention that has a very fast effect simulating the efficacy of an Emulsion Concentrate (in the same way, with increased wall forming materials and reduced content of surface active ingredients, eventually at lower shearing rates during emulsification, the particle sizes of our invented formulations are up to 48-50 µm; higher particle sizes are able to be obtained according our process/formulas, but they result in physical unstability of the formulation (too viscous, caking, bleeding, etc.).

The release pattern of the formulations according the invention is exemplified in the FIG. 1, wherein the microencapsulated abamectin at 1.8% resembles extremely well the release pattern of the commercial product Dynamec (Emulsion Concentrate of Abamectin at 1.8%). The trial was performed by an European Union/OECD accredited laboratory, against *Tetranychus urticae* present in the crop *Cucumis sativus*; with foliar application of 1000 L/Ha on the leaves and at a mixing of 17.5 mL of formulation/100 L of water (0.7 N) and 25 mL of formulation/100 mL of water (1 N—nominal—). It can be appreciated that the distribution pattern of the spider mite is exactly the same (considering obvious field uncontrollable variations), of the 0.7 N of Example 1 and the 1.0 N dose of the Dynamec. Not only that: the microencapsulated abamectin, offers better activity, being comparable our 0.7 N dosage with the 1 N of Dynamec, much more than probably due to the stability given by the microencapsulation, and the surfactant characteristics of our formulation. After 14 days, residues of abamectin components on leaves and fruits presented no statistically significant differences.

Note the extremely homogeneous and small particle size as shown in FIG. 5.

For extended release of abamectin the skilled in the art will decrease the amount to carbohydrate hydrocolloids, increase the particle size by a lower shearing stress during microencapsulation and using from 2 to 5 times more wall forming material as that used in example 1.

Examples and Conclusions Regarding UV and Oxidation Stability of the Macrolide lactone.

By the chemical similarity of abamectin with other macrolide lactones, it is very reasonable to extend our results (in the absence of any known moieties that would make other mectins significantly and inequivocally resistant to UV and oxidation) done with abamectin for all the rest of known macrolide lactones of industrial use.

We have performed a series of tests exemplified in the FIGS. 2, 3 and 4, using the formulation of Example 1 and a commercial formulation of abamectin at 1.8%.

In order to analyze the stability of abamectin in the formulations, 200 µg of formulation were put into a beaker. 1.2 mL acetonitrile (ACN) and 0.4 mL 2-propanol (i-PrOH) were added. The mixture was homogenized by shaking and submitted to LC-MS/LC-UV analysis (248 nm).

The test can be carried out in any laboratory, having in mind that what is of interest is the relative differences in between the two types of formulations (microcapsules according this invention and an emulsion concentrate not object of the present invention). Notable, there is still no commercial microencapsulated abamectin product 25 in the market, to the best knowledge of the authors, thing that contributes to proof the difficulty in performing a functionally good CS (Capsule Suspension) formulation of abamectin (the formulation of Example 1, and modifications thereof within the scope of the claims are conform regarding CS Specifications of the FAO/WHO for plant protection products). We have observed that the UV-protection naturally given by the lignosulfonates is not directly related with their few content in the formulation, being the protection against UV a synergistic effect of the claimed coformulants.

The irradiation test is done irradiating, in an opened beaker of 10 cm diameter, 40 mL of the suspension with a common UV light TLC-lamp at 240 nm situated on the top of the two test samples (beakers) for 240 minutes at a distance of 15 cm, and further natural sunlight exposure for 60 hours behind a glass. As we can appreciate in the comparison of FIGS. 2B and 3B, the decomposition of the macrolide lactone in the EC formulation is (exactly) 47%, while in the formulation of the example 1, this result is only 11% (an improvement of 89% to 53% of remaining avermectin B1a, namely 60% improvement over the EC of protection). When the UV-protectors of the Example 1 are added to the commercial EC in the same proportion, the decomposition in the modified EC amount still to 35% (chromatographs) not shown. Further, if to the formulation of the Example 1 we do not add the UV-protectors, the decomposition is surprisingly still only 25% (better than the EC with incorporated UV-protectors). It is to note that no commercial formulation has appeared to contain UV-protectors according to our analysis (at least those available to us), and the first reference we know of using UV-protectors in ECs of abamectin is this document itself. Therefore, we claim that according our invention, when performing the above-mentioned test, the microencapsulated formulation provides a protection versus ECs, lowering the decomposition of avermectins (or corresponding macrolide lactone) to a conservative (underestimated) 20% below that of the EC. We have observed by LC-MS that the main degradation compound of irradiated abamectin is the Z-8,9 isomer of the avermectins, as shown in FIG. 4.

Examples and Conclusions Regarding Rheological Properties.

The reader may observe that the necessary features for all embodiments of the present invention refer to independent claim 1, wherein compounds 1 d. (i and ii) are of necessary use. We have seen that they do not only help into obtaining the astonishing EC behavior, the UV protective properties of our invention, but also because other combinations without such necessary coformulants lead eventually to formation of liquid crystals and, with storage, to problems of pourability and increased viscosity.

In FIG. 6, the formulation 1 and 3 are according to the present invention and have been tested after an accelerated storage stability tests at 54° C. for 14 days. The formulation 2—not in the scope of the patent—has been done according the invention except for the use of the compounds of claim 1 d (i+ii), that have been replaced by rational amounts of other non-ionic dispersants (tristyrylphenol+polysorbitan 20; and no presence of lignosulfonates or other claimed compounds in claim 1 d i.+ii.), and the carbohydrate hydrocolloids have been replaced by acrylate protective colloids.

While right after formulation, all samples 1, 2, 3, present a nice behavior (line 4 represents the viscosity of the formulation diluted in water at 1:2, equal for all formulations), after the storage test, only the formulations 1 and 3 present an acceptable rheological behavior with quasi Newtonian behavior for low shear force and some thixotropy at higher shear rates, being the viscosity corresponding to a fluid liquid. However, the formulation 2, after the 2 weeks storage time presents problems of pourability and the formation of surfactant-related structures is the proposed reason for the increase of viscosity that makes the formulation unusable, and presents a strong thixotropic behavior (the formulation becomes liquid, but only after 10 minutes of vigorous shaking of the container). Obviously, we have performed long series of tests to select the necessary coformulants as claimed in the independent claim, not shown herein, and that, at the same time, allow the targeted release by control of particle size, and help or in the worse case, do not represent a diminishing effect of UV-protection (over that given by the simple micro encapsulation).

Example 2

Slow Release Formulation

This invention may take profit of the UV-protective synergic activity of the formulation ingredients, as well as their chemical compatibility with the mectins and its proven adequate biological activity as well as good physicochemical properties for slow release formulations of mectins. The present formulation is an example of the application of the invention for the slow release of macrolide lactones, exemplified by the microencapsulation of milbemectin (milbemicyns A3 and A4) and abamectin (avermectins $B_{1a}$ and $B_{1b}$) at a ratio by weight percent of 1:1.

Formulation of Example 2.A

|  | Parts |
| --- | --- |
| Milbemycin | 8 |
| Abamectin | 8 |
| TEGO MR2138 | 0.49 |
| Agrimer ® AL 10 | 2 |
| Carboxymetylcelullose (CMC) | 0.6 |
| Ascorbic acid | 0.3 |
| Atlox LP-1 | 2 |
| p-ocytylbenzene sulfonic acid | 0.1 |
| Sulfuric acid | 0.01 |
| BHT | 1 |
| Dibutyltindilaurate | 0.01 |
| 1,6-Hexanediamine | 0.3 |
| Germall ® II | 0.2 |
| Hostaphat ® B310 | 25 |
| Solvesso ® 100 | 11.3 |
| Powderlink ® 1174 | 2.6 |
| Propylenglycol | 2 |
| Reax 85 A | 5 |
| PAPI ® | 5 |
| Synperonic PE/L64 | 1 |
| TMXDI ® | 3 |
| Water | 32 |
| Caraya Gum | 0.1 |

The present formulation fulfils the requirements as claimed, and shows increased UV protection with respect to a customary EC formulation of Abamectin and Milbemectin as detailed below (the comparative formulation), and of course, improved homogeneicity of the particle size and physical stability of the formulation, with respect to prior art formulations.

Formulation 2.B. EC State of the Art Formulation (Not Falling in the Scope of the Invention, for Comparative Purposes):

| Compound | Parts in wt.-% |
| --- | --- |
| Abamectin technical | 10 |
| Milbemectin technical | 10 |
| Butylated Hydroxy Toluene | 0.5 |
| Cyclohexanol | 39.5 |
| Solvesso ® 100 | 20 |
| Propylene glycol | 10 |
| Escalol ® 557 | 0.01 |
| Acetic acid | 0.01 |
| Castor oil 54 mol ethoxylated | 9.98 |

The UV protection of the formulation of Example 2.A was (according the test described in Example 1) 25% better than that of the EC above, even when in the EC an UV-protector has been used: remarkably in the microencapsulated formulation, there is no UV-protector. The stability in accelerated storage stability trials (54° C. for 14 days) of the 2.A was 32% better than the stability of the EC (by HPLC-UV at 254 nm analysis).

The level of microencapsulated mectins in the example 2.B was 99.2% by wt.-% and same HPLC method). Further, in greenhouse trials, the formulation 2.8 showed no activity at all after 16 days, while formulation 3.A, was able to control the greenhouse white fly on tomatoes before ripening for as long as 35 days.

Example 3

Level of Entrapment of Mectins Compared with State of the Art Similar Process An formulation was made for comparative purposes very close to the one claimed in the present invention and method—with the formula below—and according the process of the present invention.

Formulation 3.A

| Component | Parts in wt.-% |
|---|---|
| Ivermectin | 1.83 |
| PAPI | 2 |
| 1,6-Hexanediamine | 2 |
| Reax 88 B | 2 |
| Genapol LA 070 | 15 |
| Ascorbic acid | 0.49 |
| Propyleneglycol | 10 |
| BHT | 1 |
| Atlox LP-1 | 1 |
| Titanium Dioxide UV-absorbant/reflectant) | 1 |
| Water | 41 |
| Solvesso 100 | 22.68 |

Formulation 3.B

The formulation 3.B, according to this invention, is the same as Example 1.A, wherein the abamectin has been replaced by ivermectins.

The level of entrapment of the pure ivermectin was only 61% according Formulation 3.A, being a microencapsulation based in the same reaction as ours, while according 3.B, the level of entrapment was 94.7%. This demonstrates that the degree of microencapsulation according to this invention is superior to the level of microencapsulation of a customary polyurea/polyurethane microencapsulation. We have purposedly selected 3A since is a close modification at the view of the present document of the published method of microencapsulation of the pesticide clomazone with demonstrated control of volatility (implicitly, high degree of entrapment). Moreover, with a postfacto analysis at the view of our best results, we have incorporated a UV-reflectant/absorbant as Titanium Dioxide, an antioxidant as BHT, and the massive use of lignosulfonates, in order to reduce the variables that may influence the comparison. Notably, the formulation 3.B still—according to the test of Example 1—shows better protection against UV-degradation than formulation 3.A (improvement of 22%), being both microencapsulated mectins with antioxidants and UV-protectors.

Example 4

Coformulation of Microencapsulated Macrolide Lactones with Suspended Neonicotinoids As detailed in the description, the present invention allows any possible combinations of active ingredients in so far there are no incompatibilities (chemical and/or physicochemical). An representative example is the combination of a suspension concentrate of imidacloprid and thiametoxam (at ration 1:1 wt.-%) at 15%, with microencapsulated abamectin at 3%.

For performing this combination, first, it is prepared a suspension concentrate of imidacloprid and thiametoxam with any state of the art process, at the targeted concentration. Then a microencapsulated formulation of abamectin is performed according example 1.A, wherein the active ingredient is correspondingly increased and the water reduced in the same amount. To the microencapsulated formulation of abamectin, additionally it is added any necessary surfactants to allow the good dispersion of the microcapsules in the suspension concentrate (e.g., a mixture of sodium or calcium dodecylbenzenesulfonate with tristyrilphenol ethoxylated and Atlox LP-5 at 1:1:1; representing in total 10% of the weight of the microencapsulated formulation). Finally such re-adjusted CS of abamectin is mixed with the SC of imidacloprid and thiamethoxam at a ration 1:2.

This leads to the formation of a suitable formulation ZC of macrolide lactones with neonicotinoids, specially interesting for the control of insects and mites in agriculture.

Example 5

Another embodiments of the present invention are exemplified in examples 5.A to 5.F. Examples 5.G and 5.H are not falling inside the scope of protection since they fail to provide the effects demonstrated for the claimed compositions. While the level of entrapment was for 5.A to 5.F always over 90%, in examples 5.G and 5.H the entrapment was 71% and 78% respectively. Further, we observed in our multiple tests that the use of at least sodium salt that contains naphthalene sulfonate, lignosulfonate, or succinate, sulfosuccinate groups and/or at least one a dispersant of the type alkenyl or alkanyl or alkylen pyrrolidinone polymer (of the series Agrimer®, for example) protects from the caking of the formulation and degradation of the corresponding mectin.

| | 5.A | 5.B | 5.C | 5.D | 5.E | 5.F | 5.G | 5.H |
|---|---|---|---|---|---|---|---|---|
| | Parts in weight percent | | | | | | | |
| Zeta-cypermethrin | 0 | 5 | 3 | 25 | 0 | 0 | 0 | 0 |
| Imidacloprid | 10 | 5 | 3 | 0 | 0 | 0 | 10 | 0 |
| Abamectin | 2 | 5 | 3 | 1 | 20 | 0.1 | 2 | 0.1 |
| Silicone Antifoam | 0.1 | 0.1 | 0.1 | 0.1 | 0 | 0.1 | 0.1 | 0.1 |
| Agrimer ® AL 25 | 2 | 2 | 2 | 1 | 0 | 0.3 | 0 | 0 |
| Naphalene formaldehyde condensate | 0.6 | 0 | 0 | 0.1 | 3 | 0.1 | 0 | 0 |
| Ascorbic acid | 0.3 | 0.3 | 0.3 | 0 | 0.2 | 0.1 | 0.3 | 0.1 |
| Atlox LP-1 | 2 | 2 | 2 | 1 | 0 | 0 | 2 | 0 |
| p-Dodecylbenzene sulfonic acid | 0.1 | 0.1 | 0.1 | 0 | 0.02 | 0 | 0 | 0 |
| Sulfuric acid | 0 | 0 | 0 | 0.05 | 0 | 0.1 | 0 | 0.1 |
| BHT | 1 | 1 | 0.1 | 0 | 0.1 | 0 | 1 | 0 |
| Zinc Oxide | 1 | 1 | 0 | 0 | 0.3 | 0 | 1 | 0 |
| Escalol ® 556-Benzophnone type | 0 | 0 | 0 | 0 | 0.5 | 5 | 0 | 5 |
| Dibutyltindilaurate | 0.01 | 0.01 | 0.01 | 0 | 0 | 0.03 | 0.01 | 0.03 |
| Genapol ® 0 100 | 4 | 3 | 3 | 4 | 0 | 1 | 9 | 1 |
| 1,6-Hexanediamine | 0 | 0 | 0 | 0.6 | 0 | 0.2 | 0 | 0.2 |
| Ethylenediamine | 0.3 | 0.3 | 0.3 | 0.1 | 0.2 | 0 | 0.3 | 0 |
| Germall ® II | 0 | 0 | 0 | 0.01 | 0 | 0 | 0 | 0 |
| Hostaphat ® B310 | 26 | 10 | 10 | 0 | 10 | 0 | 26 | 0 |
| Solvesso ® 100 | 6 | 0 | 0 | 0 | 0 | 0 | 6 | 0 |
| Powderlink ® 1174 | 1 | 1 | 1 | 0.1 | 3 | 0.2 | 1 | 0.2 |

-continued

|  | 5.A | 5.B | 5.C | 5.D | 5.E | 5.F | 5.G | 5.H |
|---|---|---|---|---|---|---|---|---|
|  | Parts in weight percent | | | | | | | |
| Propylenglycol | 0 | 0 | 0.1 | 0 | 2 | 1 | 0 | 1 |
| Proglyde ® DMM | 3 | 3 | 0 | 2 | 0 | 1 | 3 | 1 |
| m-Xylene | 0 | 0 | 0 | 10 | 3 | 0 | 0 | 0 |
| Corn Oil | 0 | 16.8 | 22 | 24 | 0 | 35.9 | 0 | 35.9 |
| PVP ® K-15 | 0.1 | 0.1 | 0 | 0.1 | 0 | 0 | 0.1 | 0 |
| Reax ®85A | 5 | 8 | 8 | 5 | 1 | 0.6 | 0 | 0.6 |
| PAPI ® | 1 | 1 | 1 | 0.8 | 0 | 0.1 | 1 | 0.1 |
| Toluene-diisocyanate | 0 | 0 | 0.7 | 1 | 0.1 | 0 | 0 | 0 |
| Isopar M | 0 | 0 | 0 | 0 | 10 | 0 | 0 | 0 |
| Synperonic PE/L64 | 1 | 1 | 1 | 0 | 3 | 0 | 3.7 | 0.4 |
| TMXDI ® | 0.5 | 0.5 | 0.5 | 0.2 | 0.1 | 0.2 | 0.5 | 0.2 |
| Water | 32 | 33 | 38 | 21.3 | 40 | 50 | 32 | 50 |
| Xanthan Gum | 0.14 | 0.14 | 0.14 | 0 | 1 | 0.9 | 0.14 | 0.9 |
| Caraya Gum | 0 | 0 | 0 | 1 | 0 | 0.1 | 0 | 0.1 |
| Arabic Gum | 0.85 | 0.5 | 0.5 | 1 | 2.48 | 1 | 0.85 | 1 |
| CMM | 0 | 0.15 | 0.15 | 0.5 | 0 | 1 | 0 | 1 |
| Carrageen | 0 | 0 | 0 | 0.1 | 0 | 1 | 0 | 1 |

After the performance of the examples referred in the present document, and additional trials until the inventors arrived to the proposed solution, we conclude that the quantity of the polymeric material must be at least 10% of the quantity of the mectin to microencapsulate in order to achieve the necessary UV-protection due to the protecting effect of the wall. Ideally, and apart from the content of active ingredients, the quantity of wall forming material used in the reaction that makes the wall should be 1-8% of the total weight of the formulation.

The presence of the carbohydrate or modified carbohydrate hydrocolloids increases the UV-protection and it is necessary to solve simultaneously the problem of caking, with the condition that at least one of the hydrocolloid is known as a gum for the skilled in the art, most preferably Arabic gum, Xanthan gum and/or Caraya gum. The best results to prevent caking have been obtained with the simultaneous use of Xanthan gum and Arabic gum at at least. Preferably, the total content of Arabic gum is 0.25-3% and Xanthan gum is 0.1-3%. Surprisingly, the dispersants of the type (a) alkenyl or alkanyl or alkylen pyrrolidinone polymer and/or derivatives thereof present, apart from a improvement of the pourability of the formulations of mectins, an marked effect on the UV-protection; being the effect of protection of these compounds not only additive with the thickness of the wall: this is suggested to the property of the double bonds of such polymers to be activated forming radicals before the light affects the mectins, and apparently, such radicals stabilized in the big macroestructures of such polymers. The effect of UV-protection may be obtained as well with other polymers (b) as naphthalene sulfonate, naphthalene formaldehyde condensates, lignosulfonate, sulfomethylated lignosulfonate or succinate, sulfosuccinate groups; and/or derivatives thereof, being preferred a combination of lignosulfonates (more preferably sulfomethylated) with alkylen pyrrolidinone polymers for increasing synergistically the UV-protective effect of our invention namely to add UV-protection over the expected increase due only to the wall thickness of the microcapsules—. Note that the use of alkylen pyrrolidone polymers over 15% has been shown not to increase the UV protective action and to make the formulation relatively unstable to physical stability, in particular to bleeding and caking. Below the use of 0.2% of the mentioned pyrrolidone polymers (a) or below the use of 0.5% (note the higher lower limit) of the other proposed polymers (b), there is no substantial effect on the UV-protection, and only a slight effect on the physical stability of the formulation. In another level, in order to achieve a 90% of entrapment of the mectins, the above mentioned ratios are appropriated for such surface active compounds.

Remarkably, the narrow distribution of particle sizes (referred as homogeneicity, not necessarily as small particle size) cannot be achieved when the total ratio of oil solvent to water is outside of the ranges 5:95 (this lower limit for very diluted charge of active ingredient, e.g., 0.05 to 0.3%) to 70:30. Otherwise, it cannot be obtained the simultaneous improvements of the present invention.

Particularly excellent rheological properties have been found using exclusively vegetable oils (and modifications thereof, as corn oil, soya oil, methyl cocoate) and/or Hostaphat B310, wherein the best properties for prevention of thixotropy are with vegetable oils.

Claim 1 reflects the novel (nowhere it is described any formulation with such ingredients in the mentioned ranges) and unitary characteristics of all the claimed formulations that solve the different problems presented by this type of formulations, wherein the inventiveness is not only the limited ranges proposed, but also thanks to the proposed combinations: in between the millions of possible microencapsulation compositions we demonstrate that such purposively selected compositions lead to the desired solution to the problems addressed. Dependent claims will help to find the best embodiments within the working formulations. The spirit of the invention comprises as well obvious substitutions of coformulants or secondary active ingredients by others, chemically and functionally known to be replacements of the claimed ones, for the skilled in the art at the time of filing this patent.

The invention claimed is:

1. A method for protecting a plant with a macrolide lactone comprising applying to the plant a controlled-release microcapsule, each microcapsule enclosing at least one macrolide lactone(s), wherein the microcapsules have an average particle size of 0.5-2 μm with 90% of the particle sizes are below 15 μm, whereby, simultaneously:
   (a) dermal and acute toxicity of the controlled-release microcapsule is less than that of an emulsion of the same macrolide lactone(s) having the same concentration of the macrolide lactone(s) as the controlled-release microcapsule;
   (b) UV and visible degradation of the macrolide lactone in the controlled-release microcapsule is less than that of an emulsion of the same macrolide lactone(s) having the same concentration of the macrolide lactone(s) as the controlled-release microcapsule;
   (c) the controlled-release microcapsules have an increased biological effect than that of an emulsion of the same macrolide lactone(s) having the same concentration of the macrolide lactone(s) as the controlled-release microcapsule; and
   (d) the corresponding macrolide lactone(s) are microencapsulated with an efficiency of 90% or more.

2. The method according to claim 1, wherein the macrolide lactone(s) is coformulated with at least one or more biologically active ingredient(s), wherein the biologically active ingredient(s) is present inside and/or outside the microcapsules.

3. The method according to claim 1, wherein the macrolide lactone(s) are selected from the group consisting of: avermectins, ivermectins, mylbemicins, •macrolide antibiotics, and derivatives thereof that maintain the biological activity of the parent compounds to a lesser or higher extent and the macrolide lactones are metabolites of *Streptomyces* sp. that have antihelmintic and/or acaricide and/or insecticide properties.

4. The method according to claim 3, wherein the at least one macrolide lactone is a mixture of avermectins B1a and B1b.

5. The method according to claim 4, wherein the mixture of avermectins B1a and B1b is abamectin.

6. The method according to claim 1, wherein each microcapsule encloses only one macrolide lactone.

7. The method according to claim 6, wherein the macrolide lactone is abamectin.

8. The method according to claim 1, wherein the macrolide lactone(s) is combined with active ingredients selected from the group consisting of: fungicides, insecticides, herbicides, nematicides, miticides, acaricides, plant growth regulators and antibiotics.

9. The method according to claim 1, wherein the plant is protected against *Cacopsylla gyri, Cacopsylla, Psilidae* gen. sp., *Cydia pomonella, Phtorimaea operculella, Phtorimaea* spp., *Plutella xylostella, Plutella* sp., *Tetranychus urticae, Tetranychus kanzawai, Tetranychus* ssp., *Panonychus citri, Panonychus* ssp., *Panonychus* spp., *Aculops pelekassi, Aculops* spp., *Bursaphelenchus xylophilus, Bursaphelenchus* ssp., *liriomyza huidobrensis, Liriomyza trifolii, Liriomyza* spp. and leaf miners, red spiders, and sucking arthropods in general.

10. The method according to claim 2, wherein the at least one or more biologically active ingredient(s) is selected form the group consisting of: helminticides, nematocides, acaricides, miticides, insecticides, herbicides, fungicides, plant growth regulators, bactericides (antibiotics) and biocides for small animals.

11. The method according to claim 10, wherein the at least one or more biologically active ingredient(s) is selected from the list consisting of: (1) organophosphorous compounds as acephate, azinphosmethyl, cadusafos, chlorethoxyfos, chlorpyrifos, coumaphos, dematon, demeton-5-methyl, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion, mevinphos, monocrotophos, parathion, phorate, phosalone, phosmet, phosphamidon, phosphocarb, phoxim, profenofos, propaphos, propetamphos, prothiofos, pyrimiphos-methyl, pyrimiphos-ethyl, quinalphos, sulprofos; tebupirimphos, temephos, terbufos, tetrachlorvinphos, thiafenox, thiometon, triazophos, and trichlorphon; (2) carbamates such as aldicarb, bendiocarb, benfuracarb, bensultap, BPMC, butoxycarbocim, carbaryl, carbofuran, carbosulfan, cloethocarb, ethiofencarb, fenobucarb, furathiocarb, methiocarb, isoprocarb, methomyl, oxamyl, pirimicarb, promecarb, propoxur, thiodicarb, and thiofurox; (3) pyrethroids such as acrinathrin, allethrin, beta-cyfluthrin, bifenthrin, bioresmethrin, cyfluthrin; cyhalothrin; lambda-cyhalothrin; gammacyhalothrin, cypermethrin; alpha-cypermethrin; zeta-cypermethrin; deltamethrin, esfenvalerate, fenvalerate, fenfluthrin, fenpropathrin, flucythrinate, flumethrin, fluvalinate, tau-fluvalinate, halfenprox, permethrin, protrifenbute, resmethrin, silafluofen, tefluthrin, tetramethrin, tralomethrin, fish safe pyrethroids for example ethofenprox, natural pyrethrin, tetramethrin, s-bioallethrin, fenfluthrin and prallethrin; (4) acylureas, other types of insect growth regulators and insect hormone analogs such as buprofezin, chromfenozide, chlorfluazuron, diflubenzuron, fenoxycarb, flufenoxuron, halofenozide, hexaflumuron, hydroprene, lufenuron, methoprene, methoxyfenozide, novaluron, pyriproxyfen, teflubenzuron and tebufenozide, N[3, 5-dichloro-2-fluoro-4-(1,1,2,3,3,3-hexafluoropropoxy)phenyl]-N' (2,6-difluorobenzoyl) urea; (5) neonicotnioids and other nicotinics such as acetamiprid, AKD-1022, cartap, T1-435, clothianidin, MTI-446, dinotefuran, imidacloprid, nicotine, nitenpyram, thiamethoxam, thiacloprid; (6) macrolides such as avermectins, milbemycins, for example such as abamectin, ivermectin, milbemycin, emamectin benzoate; and (7) other insecticidal, acaricidal, mollusquicidal and nematocidal compounds or actives such as aldrin, amitraz, azadirachtin, azocyclotin, bifenazate, bromopropylate, chlordimeform, chlorfenapyr, clofentezine, chlorobenzilate, chlordane, cyhexatin, cyromazin, DDT, dicofol, dieldrin, DNOC, endosulfan, ethoxazole, fenazaquin, fenbutatin oxide, fenproximate, beta-fenpyroximate, fipronil, flubenzimine, hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodidofen, sulfur, tebufenpyrad, tetradifon, triazamate, an insect-active extract from a plant; a preparation containing insect-active nematodes, a preparation obtainable from *Bacillus subtilis, Bacillus thuringiensis*, a nuclear polyhedrosis virus, or other like organism genetically modified or native, as well as synergists such as piperonyl butoxide, sesamax, safroxan and dodecyl imidazole.

* * * * *